United States Patent
Gilman

(10) Patent No.: US 9,725,724 B2
(45) Date of Patent: Aug. 8, 2017

(54) NEUTRAL NUCLEIC ACID LIGANDS

(71) Applicant: Vivonics, Inc., Waltham, MA (US)

(72) Inventor: Vladimir Leo Gilman, Westford, MA (US)

(73) Assignee: Vivonics, Inc., Waltham, MA (US)

(*) Notice: Subject to any disclaimer, the term of this patent is extended or adjusted under 35 U.S.C. 154(b) by 378 days.

(21) Appl. No.: 14/278,159

(22) Filed: May 15, 2014

(65) Prior Publication Data

US 2014/0343264 A1 Nov. 20, 2014

Related U.S. Application Data

(60) Provisional application No. 61/824,213, filed on May 16, 2013.

(51) Int. Cl.
  C07H 21/04 (2006.01)
  C07H 19/04 (2006.01)
  C12N 15/115 (2010.01)

(52) U.S. Cl.
  CPC ........ *C12N 15/115* (2013.01); *C12N 2310/16* (2013.01); *C12N 2310/311* (2013.01); *C12N 2310/3517* (2013.01); *C12N 2320/52* (2013.01)

(58) Field of Classification Search
  CPC .................................................. C12N 15/115
  USPC .................................. 536/23.1, 26.6; 544/44
  See application file for complete search history.

(56) References Cited

U.S. PATENT DOCUMENTS

| | | |
|---|---|---|
| 4,739,044 A | 4/1988 | Stabinsky |
| 4,757,141 A | 7/1988 | Fung et al. |
| 5,270,163 A | 12/1993 | Gold et al. |
| 5,660,985 A | 8/1997 | Pieken et al. |
| 6,818,395 B1 | 11/2004 | Quake et al. |
| 7,169,560 B2 | 1/2007 | Lapidus et al. |
| 7,282,337 B1 | 10/2007 | Harris |
| 7,476,734 B2 | 1/2009 | Liu |
| 7,678,894 B2 | 3/2010 | Siddiqi |
| 7,767,805 B2 | 8/2010 | Buzby |
| 8,236,570 B2 | 8/2012 | Gilman |
| 2002/0164629 A1 | 11/2002 | Quake et al. |
| 2007/0060536 A1* | 3/2007 | Gao ............... C07F 9/2408 514/44 A |
| 2011/0104667 A1 | 5/2011 | Gilman |

OTHER PUBLICATIONS

Jayasena, "Aptamers: An Emerging Class of Molecules That Rival Antibodies in Diagnostics," Clin. Chem. 45 (9):1628-1650, 1999.
Sponer J, Leszczynski J, Hobza P. Electronic properties, hydrogen bonding, stacking, and cation binding of DNA and RNA bases. Biopolymers. 2001-2002;61(1):3-31.
André C, Xicluna A, Guillaume YC. Aptamer-oligonucleotide binding studied by capillary electrophoresis: cation effect and separation efficiency. Electrophoresis. Sep. 2005;26(17):3247-55.
Sanger et al. "DNA Sequencing with Chain-terminating inhibitors," Proc Natl Acad Sci USA, 74(12): 5463 67, 1977.

(Continued)

*Primary Examiner* — Jezia Riley
(74) *Attorney, Agent, or Firm* — Brown Rudnick LLP; Thomas C. Meyers

(57) ABSTRACT

The invention generally relates to isolated nucleic acid ligands that are neutral under physiological conditions.

9 Claims, 2 Drawing Sheets

(56) References Cited

OTHER PUBLICATIONS

Maxam et al. "A new method for Sequencing DNA," Proc. Natl. Acad. Sci., 74: 560-564, 1977.
Braslaysky, et al., "Sequence information can be obtained from single DNA Molecules," PNAS (USA), 100: 3960-3964, 2003.
Kambara et al. "Optimization of Parameters in a DNA Sequenator Using Fluorescence Detection," BiolTechnol., 6:816-21, 1988.
Baldrich et al.,"Aptasensor Development: Elucidation of Critical Parameters for Optimal Aptamer Performance," Anal. Chem. 2004;76(23):7053-7063.
Smith et al. "The synthesis of oligonucleotides containin ganaliphaticamino group at the 5'terminus: synthesis of fluorescent DNA primers for use in DNA sequence analysis" Nucl. Acid Res., 13:2399-2412, 1985.
Smith et al. "Flourescence detection in automated DNA Sequence Analysis" Nature, 321: 674-679, 1986.
Sharma et al. "A general method for the synthesis of 3'-sulfhydryl and phosphate group containing oligonucleotides" (Polynucleotides Res., 19:3019, 1991).
Giusti et al. (PCR Methods and Applications, 2:223-227, 1993).

Agrawal et al. "Site-Specific Functionalization of Oligodeoxynucleotides for Non-Radioactive Labelling "(Tetrahedron Letters, 31:1543-1546, 1990).
Sproat et al. "The synthesis of prtected 5'-mercapto-2',5'-dideoxyribonucleoside-3'-O-phosphoramidites; uses of 5'-mercapto-oLigodeoxyribonucleotides" Polynucleotides Res. ,15:4837, 1987.
Nelson et al. "Bifunctional oligonucleotide probes synthesized using a novel CPG support are able to detect single base pair mutations" Polynucleotides Res.,17:7187-7194, 1989.
Sokolowska M, Czapinska H, Bochtler M. Hpy188I-DNA pre- and post-cleavage complexes—snapshots of the GIY-YIG nuclease mediated catalysis. Nucleic Acids Res. Mar. 2011;39(4):1554-64.
Nowotny M, Gaidamakov SA, Crouch RJ, Yang W. Crystal structures of RNase H bound to an RNA/DNA hybrid: substrate specificity and metal-dependent catalysis. Cell. Jul. 1, 2005;121(7):1005-16.
Misra, V. et al. "Electrostatic Contributions to the Binding Free Energy of the lcI Repressor to DNA," Biophysical Journal, vol. 75, Nov. 1998, pp. 2262-2273.
Musumeci, D. et al. "Polyvalent nucleic acid aptamers and modulation of their activity: a focus on the thrombin binding aptamer," Pharmacology & Therapeutics 126 (2012) pp. 202-215.

* cited by examiner

NEUTRAL NUCLEIC ACID LIGANDS

RELATED APPLICATION

The present application claims the benefit of and priority to U.S. provisional application Ser. No. 61/824,213, filed May 16, 2013, the content of which is incorporated by reference herein in its entirety.

FIELD OF THE INVENTION

The invention generally relates to isolated nucleic acid ligands that are neutral under physiological conditions.

BACKGROUND

A nucleic acid ligand (aptamer) is a nucleic acid macromolecule (e.g., DNA or RNA) that binds tightly to a specific molecular target. Like all nucleic acids, a particular nucleic acid ligand may be described by a linear sequence of nucleotides (A, U, T, C and G), typically 15-40 nucleotides long. In solution, the chain of nucleotides forms intramolecular interactions that fold the molecule into a complex three-dimensional shape. The shape of the nucleic acid ligand allows it to bind tightly against the surface of its target molecule, generally binding their targets with very high affinity, e.g., the majority of anti-protein nucleic acid ligands have equilibrium dissociation constants in the picomolar to low nanomolar range.

However, high affinity does not guarantee specificity. Even with high affinity aptamers, non-specific binding or cross-reactivity is a problem (Commercialization of an Aptamer-Based Diagnostic Test, 2012; Andy Ellington's Blog, 2011; Van Simaeys, 2010; Li, 2009; Rahimi, 2009).

SUMMARY

The invention recognizes that aptamer non-specific binding is caused by significant negative electrostatic charge of an aptamer under physiological conditions. The negative charge comes from phosphate residues connecting individual nucleosides of an aptamer sequence. Thus, aptamers non-specifically bind various positively charged species found in biological samples. That is especially true if the positively charged species are present at levels exceeding those of an anticipated target, which can easily be affected by slight changes in pH and salinity, both of which are common in complex biological fluids.

Accordingly, the invention provides isolated and synthesized nucleic acid ligands that are neutral under physiological conditions. Aspects of the invention are accomplished by neutralizing the phosphate residues connecting individual nucleosides of the aptamers. Any neutralizing chemistry may be used, and a preferred chemistry is modifying the phosphodiester bond to be a phosphotriester bond. That chemical modification of the phosphate group connecting nucleosides of the aptamer sequence is useful for elimination of the non-specific binding of aptamers.

Additionally, when exposed to natural environments and until bound to their anticipated targets, the aptamers can be degraded by naturally present enzymes (RNAses and DNAses) that attack the phosphodiester linkages connecting the individual nucleosides. Aptamers of the invention that do not have phosphodiester bonds therefore have increased stability under conditions of potential enzymatic attack.

The nucleic acid ligands may be single stranded or double stranded. The nucleic acid ligands may be DNA or RNA. The nucleic acid ligands may be linked to other molecules. The linkage may be by any method known in the art. The linkage may be a cleavable linkage. For example, nucleic acid ligands of the invention may be linked to a detectable label, such as an optically detectable label, such as a fluorescent label. In other embodiments, nucleic acid ligands of the invention may be linked to a drug.

Another aspect of the invention provides a nucleic acid ligand having repeating units of Formula I:

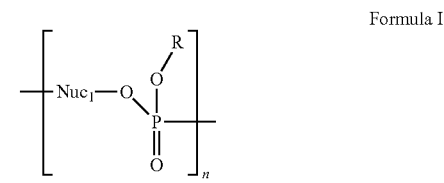

in which $Nuc_1$ is a naturally or non-naturally occurring nucleoside that may be the same or different for each unit; R is the same or different for each unit and is selected from the group consisting of a fatty acid, a sugar, an amino sugar, an amino acid, and a sialic acid; and n is an integer greater than 1. In certain embodiments, $Nuc_1$ is a deoxyribonucleoside. In other embodiments, $Nuc_1$ is a ribonucleoside.

DETAILED DESCRIPTION

Figure 1:
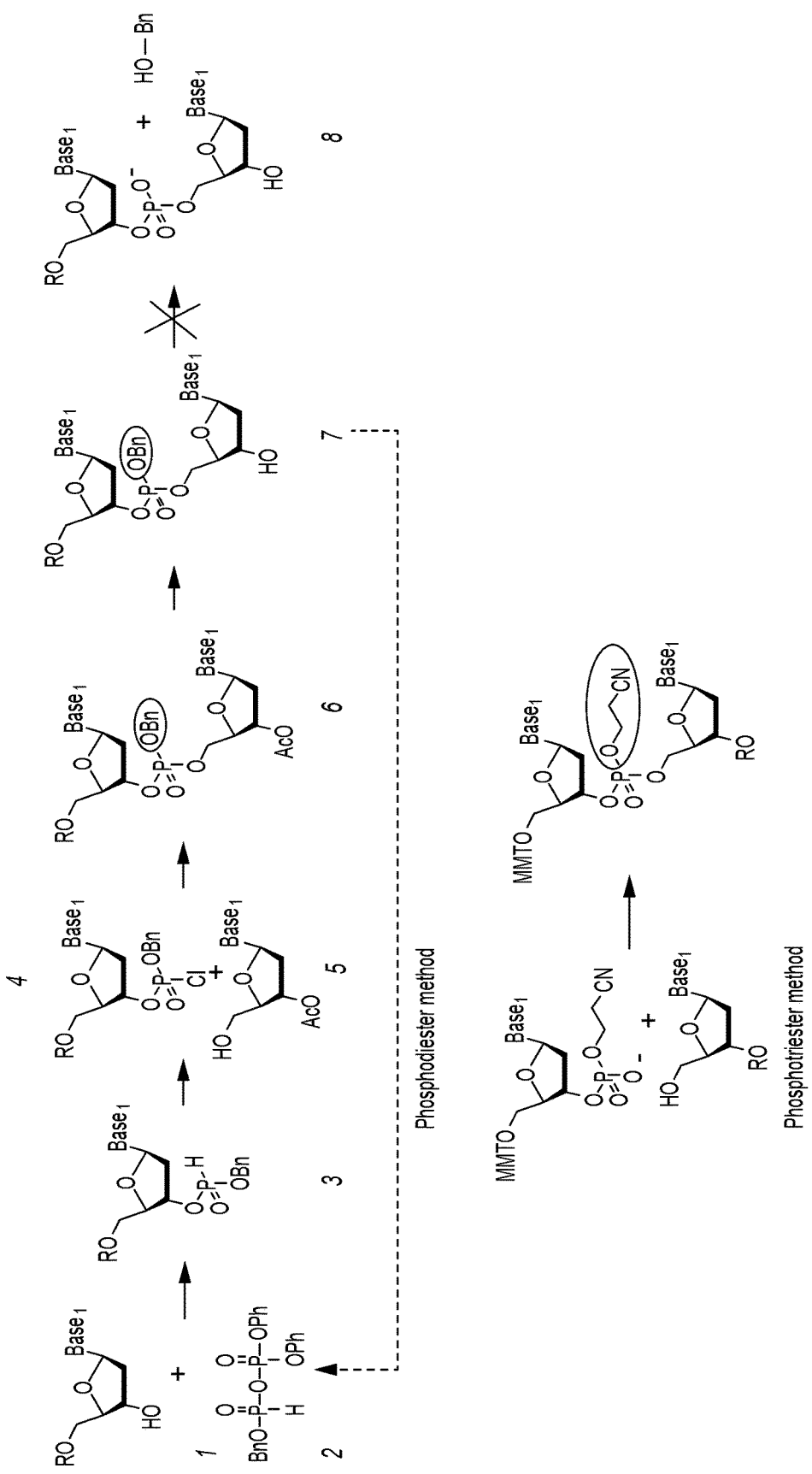
FIG. 1 is a schematic of a protocol for synthesizing an aptamer of the invention.

The invention generally relates to isolated and synthetically synthesized nucleic acid ligands that are neutral under normal physiological conditions in the human body. In certain embodiments, nucleosides of the ligand are linked via phosphotriester bonds instead of phosphodiester bonds. In that manner, the negative charge of the phosphate group that is typically present between nucleotides in a chain is removed.

A nucleic acid ligand (aptamer) is a nucleic acid macromolecule (e.g., DNA or RNA) that binds tightly to a specific molecular target Like all nucleic acids, a particular nucleic acid ligand may be described by a linear sequence of nucleotides (A, U, T, C and G), typically 15-40 nucleotides long. Binding of a nucleic acid ligand to a target molecule is not determined by nucleic acid base pairing. See, for example, Jayasena, Clin. Chem. 45(9):1628-1650, 1999 and Baldrich et al., Anal. Chem. 2004; 76(23):7053-7063. In solution, the chain of nucleotides forms intramolecular interactions that fold the molecule into a complex three-dimensional shape. The shape of the nucleic acid ligand allows it to bind tightly against the surface of its target molecule. Nucleic acid ligands generally bind their targets with very high affinity, e.g., the majority of anti-protein nucleic acid ligands have equilibrium dissociation constants in the femtomolar to low nanomolar range.

Neutral refers to aptamers with no electric charge, i.e., no moiety in the aptamer possesses a charge under physiological conditions. Without being limited by any particular theory or mechanism of action, it is believed that the benefits of covalent modification of the phosphoester moieties of the nucleic acid backbone cannot be achieved by simple offsetting negative charges of the nucleic acid backbone via a counter ion complexation of phosphate or via covalent modification of nucleosides with positively charged functions. Indeed, the anionic character of nucleic acids under normal physiological conditions is caused by ionization of the non-esterified acidic functionalities of the nucleic acid backbone. Thus, in solution, under normal physiological conditions, the anionic nucleic acid backbone is surrounded by a number of counter ions. If the negative charge of the individual phosphodiester bonds are neutralized by forming complexes with less dissociative counter ions or by increasing concentration of common counter ions, significant changes of the DNA conformation will occur (Sponer J, Leszczynski J, Hobza P. Electronic properties, hydrogen bonding, stacking, and cation binding of DNA and RNA bases. Biopolymers. 2001-2002; 61(1):3-31). Thus, if one used a library of these complexes for aptamer isolation, then exactly the same conditions resulting in formation of those oligo-counter ion complexes would have to be used for practical applications of the aptamers.

However, as biological fluids have variable compositions, it seems difficult to reproduce the same conformations of oligo-counter ion complexes in in vitro diagnostics, and, it seems unrealistic to expect the conformations of oligo-counter ion complexes used in the process of the aptamer selection to be retained in in vivo situations.

It is noteworthy to mention, that it has been also observed that the affinity of aptamers may significantly change as a function of pH and salinity (André C, Xicluna A, Guillaume Y C. Aptamer-oligonucleotide binding studied by capillary electrophoresis: cation effect and separation efficiency. Electrophoresis. 2005 September; 26(17):3247-55). Thus, it seems that other (non-covalent) chemistry of the phosphate negative charge "quenching" would not be able to achieve the same result as covalently "quenching" the free acidic moieties during the oligonucleotide synthesis, but only via formation of their esters can it be achieved.

Furthermore, the oligonucleotide molecule is essentially a polyionic compound, in which the anionic charge of the nucleic acid backbone is neutralized in solution by loosely associated counter ions. If the oligonucleotide is functionalized with as many positively charged functions as it has free acidic functionalities that offset the negative charge, the resultant molecule will most probably acquire a zwitterion configuration. In turn, these zwitterionic macromolecules can exhibit certain undesirable properties for aptamers by participating in collective intermolecular interactions. For example, the positively charged functions can bind negatively charged non-aptamer environmental biomolecules and the unaffected chemically positive functionalization of the oligonucleotide phosphate anions of the nucleic acid backbone can bind the positively charged environmental biomolecules. Essentially, in some respect, the capability of the oligonucleotide for non-specific binding will be effectively doubled. The oligonucleotides can form (self-assemble) supra-molecular layered structures. This will effectively reduce the apparent aptamer concentration (activity) and, thus, require higher aptamer doses for a desired response. Thus, it seems that off-setting the negative charge of an oligonucleotide by giving another portion of the aptamer a positive charge could not result in the same benefits for the aptamer development as eliminating the negative charge of the each of the free phosphate group via esterification.

Normal physiological conditions in the human body refers to normal conditions within mammalian tissue or body fluid under which biological reactions occur in the absence of environmental stressors. Normal Physiological conditions are generally a pH of about 7 to about 8, preferably between 7.3 and 7.6, and a temperature of about 35° C. to about 38° C., preferably 37° C. The normal concentration of sodium in the blood plasma is 136-145 mM.

In certain embodiments, nucleosides of the ligand are linked via phosphotriester bonds instead of phosphodiester bonds. In that manner, the negative charge of the phosphate group that is typically present between nucleotides in a chain is removed. Such aptamers can be produced in a completely synthetic manner. Alternatively, naturally occurring aptamers may be isolated and then chemically modified. Naturally occurring nucleic acid ligands can be identified using any methods known in the art, such as SELEX as described in Gold et al. (U.S. Pat. No. 5,270,163). Other nucleic acid ligand isolation methods are shown in Gilman (U.S. Pat. No. 8,236,570 and U.S. patent application publication No. 20110104667). Isolation of aptamers of the invention is described below.

After separation, the nucleic acid ligands of the invention may be sequenced. Sequencing may be by any method known in the art. See for example Sanger et al. (Proc Natl Acad Sci USA, 74(12): 5463 67, 1977), Maxam et al. (Proc. Natl. Acad. Sci., 74: 560-564, 1977), and Drmanac, et al. (Nature Biotech., 16:54-58, 1998), which references describe exemplary conventional ensemble sequencing techniques. Also see Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., (PNAS (USA), 100: 3960-3964, 2003), which references describe exemplary single molecule sequencing by synthesis techniques. The contents of each of the references is incorporated by reference herein in its entirety.

Whether synthetically synthesized or isolated from a natural environment, the following protocol, as shown in FIG. 1, can be used to form the phosphotriester bond. The protocol in FIG. 1 is a standard protocol in nucleic acid synthesis of forming phosphodiester bonds between nucleoside residues in a chain. In the phosphodiester method, phosphotriesterified oligonucleotides (7) are generated by reacting a 3'-(benzyl phosphochloridate) 5'-protected nucleoside (4) with a 3'-O-acetylnucleoside (4) with formation of 3'-O— acetylated posphotriesterified dinucleotide (6) and deacetylation of the latter. Also shown are auxiliary reactions of formation of precursors via reaction of 5'-protected nucleoside (1) with tribenzyl pyrophosphate (2) resulting in a 3'-(benzyl phosphate) 5'-protected nucleoside (3), which is then converted into 3'-(benzyl posphochloridate) 5'-protected nucleoside (4). If the current reaction scheme is followed through, deblocking of (7) results in formation of a functional dinucleotide (8). However, as shown in FIG. 1, the traditional synthetic procedure is stopped at the point of accumulation of the phosphotriester bond, and the final deblocking reaction is not performed, thus resulting in a neutral aptamer in which phosphotriester bonds link nucleosides in the aptamer chain.

In certain embodiments, the resulting nucleic acid ligands of the invention have repeating units of Formula I:

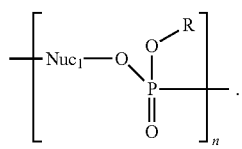

Formula I

In Formula I, n is an integer greater than 1. For example, n can be 2, 3, 4, 5, 10, 15, 20, 25, 30, 40, 50, 60, 70, 80, 90, 100, 200, 300, 500, 1000 etc., and any number between those exemplified numbers. In Formula I, $Nuc_1$ is a naturally or non-naturally occurring nucleoside that may be the same or different for each unit. In certain embodiments, $Nuc_1$ is a deoxyribonucleoside. In other embodiments, $Nuc_1$ is a ribonucleoside. Non-naturally occurring nucleic acids are known in the art and include nucleic acid analogs and derivatives, such a locked nucleic acids and peptide nucleic acids. Exemplary nucleotide analogs include morpholine, xanthine or hypoxanthine, 5-bromouracil, 2-aminopurine, deoxyinosine, or methylated cytosine, such as 5-methylcytosine, N4-methoxydeoxycytosine, and the like. Also included are bases of polynucleotide mimetics, such as methylated nucleic acids, e.g., 2'-O-methRNA, peptide nucleic acids, locked nucleic acids, modified peptide nucleic acids, and any other structural moieties that act substantially like a nucleotide or base, for example, by exhibiting base-complementarity with one or more bases that occur in DNA or RNA. Other exemplary non-naturally occurring nucleic acids are described for example in Lapidus (U.S. Pat. No. 7,169,560), Liu et al., (U.S. Pat. No. 7,476,734), Siddiqi (U.S. Pat. No. 7,678,894), and Buzby (U.S. Pat. No. 7,767, 805), the content of each which is incorporated by reference herein in its entirety.

The R groups off of the phosphortriester bond may be the same or different for each unit. The R groups off of the phosphortriester bond can be any group that can serve as a phosphodiester blocking group during the oligonucleotide synthesis (can be covalently linked to the phosphate residue connecting the phosphotriester nucleoside). Those groups can include any substances that are capable of reacting with a phosphate to form the phospho-ester bonds. For example, it is envisioned that all of the glycosylating functionalities found in O-glycosylated biomolecules can be used (e.g. fatty acids, sugars and amino sugars, sialic acids, polysaccharides, etc). In addition, the substances possessing a group capable of reacting with the phosphate, but not selected by the nature for O-glycosylation, can be used as the R groups (i.e. alcohols, aromatic alcohols, hydroxylated amino acids, unnatural sugars, peptides containing hydroxylated amino acids, neat and functionalized polyethylene glycols, etc.). It is also possible that some functionalities of these ester functionalities can also be blocked during the oligonucleotide synthesis and deblocked when the synthesis is accomplished.

The nucleic acid ligands may further include a detectable label, such as radioactive labels, chemoluminescent labels, luminescent labels, phosphorescent labels, fluorescence polarization labels, and charge labels.

In certain embodiments, the detectable label is a fluorescent label. Suitable fluorescent labels include, but are not limited to, 4-acetamido-4'-isothiocyanatostilbene-2,2' disulfonic acid; acridine and derivatives: acridine, acridine isothiocyanate; 5-(2'-aminoethyl)aminonaphthalene-1-sulfonic acid (EDANS); 4-amino-N[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'S"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescently labeled nucleotides may be obtained commercially (e.g., from NEN DuPont, Amersham, and BDL). Alternatively, fluorescently labeled nucleotides may also be produced by various techniques, such as those described in Kambara et al. (Bio/Technol., 6:816-21, 1988); Smith et al. (Nucl. Acid Res., 13:2399-2412, 1985); and Smith et al. (Nature, 321: 674-679, 1986). The fluorescent dye may be linked to the deoxyribose by a linker arm that is easily cleaved by chemical or enzymatic means. There are numerous linkers and methods for attaching labels to nucleotides, as shown in Oligonucleotides and Analogues: A Practical Approach (IRL Press, Oxford, 1991); Zuckerman et al. (Polynucleotides Res., 15: 5305-5321, 1987); Sharma et al. (Polynucleotides Res., 19:3019, 1991); Giusti et al. (PCR Methods and Applications, 2:223-227, 1993); Fung et al. (U.S. Pat. No. 4,757,141); Stabinsky (U.S. Pat. No. 4,739,044); Agrawal et al. (Tetrahedron Letters, 31:1543-1546, 1990); Sproat et al. (Polynucleotides Res., 15:4837, 1987); and Nelson et al. (Polynucleotides Res., 17:7187-7194, 1989). Extensive guidance exists in the literature for derivatizing fluorophore and quencher molecules for covalent attachment via common reactive groups that may be added to a nucleotide. Many linking moieties and methods for attaching fluorophore moieties to nucleotides also exist, as described in Oligonucleotides and Analogues, supra; Guisti et al., supra; Agrawal et al, supra; and Sproat et al., supra.

Certain chemical modifications of the nucleic acid ligands of the invention may be made to increase the in vivo stability of the nucleic acid ligand or to enhance or to mediate the delivery of the nucleic acid ligand. See, e.g., Pieken et al. (U.S. Pat. No. 5,660,985), the contents of which are incorporated by reference herein in their entirety. Modifications of the nucleic acid ligands contemplated in this invention include, but are not limited to, those that provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to 2-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping. In certain embodiments of the instant invention, the nucleic acid ligands are RNA molecules that are 2'-fluoro (2'-F) modified on the sugar moiety of pyrimidine residues.

Aptamers of the invention may also be coupled to a drug, via a binding pair, or other attachment strategies known in the art. The methods of attaching labels to the ligands may be used to attach the drug to the ligand.

Figure 2:
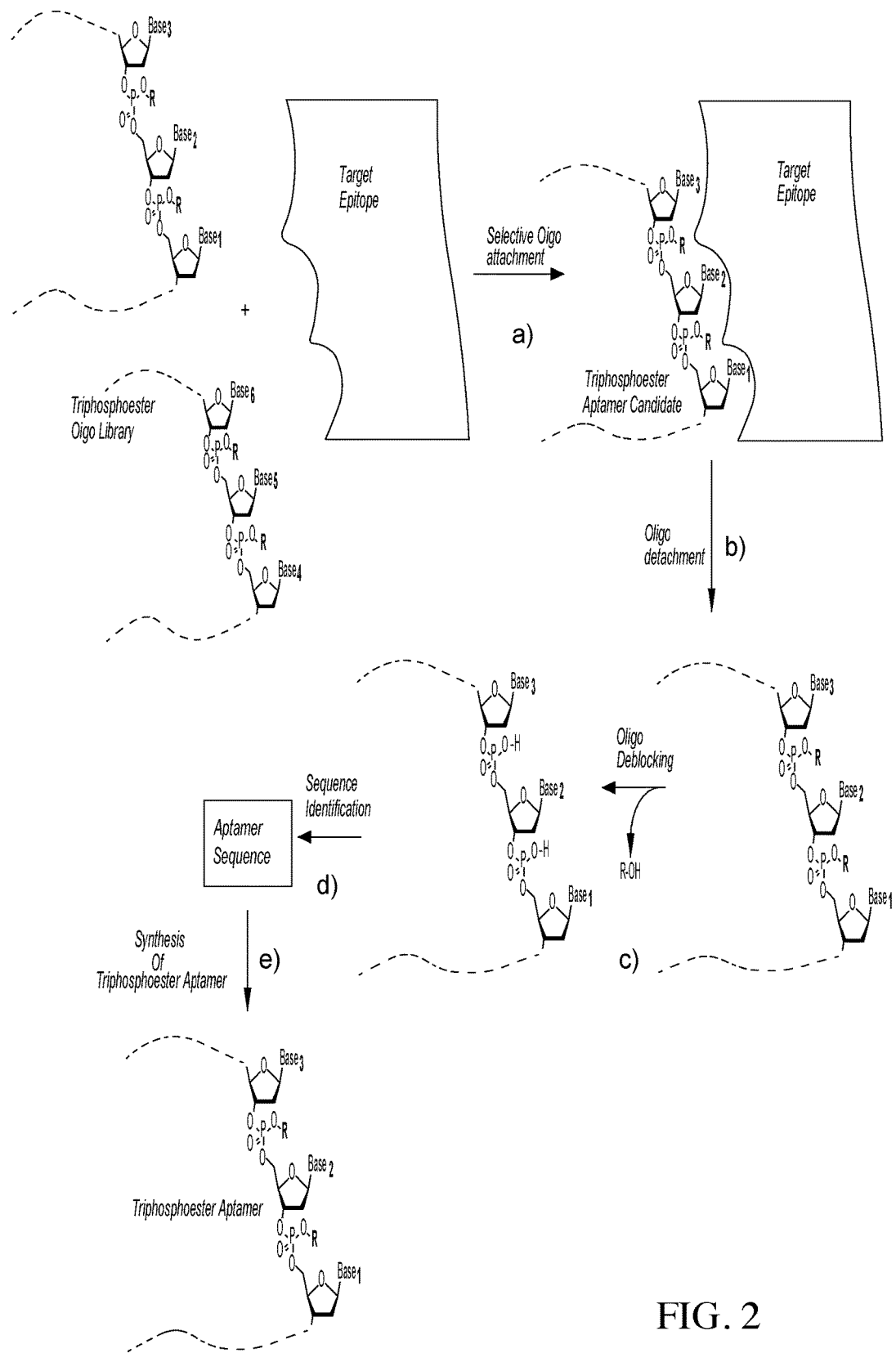
FIG. 2 is a schematic representation of a general procedure for identification of the triphosphoaptamers. In step (a), the triphosphooligo library is exposed to a desired target and an aptamer candidate is retained by an epitope of this target. Then, the aptamer candidate is detached in step (b) and deblocked in step (c). The deblocked aptamer represents now a nucleic acid oligonucleotide structure. The sequence of this oligonucleotide is then identified using common nucleic acid sequencing methods in step (d). Once the aptamer sequence is known it is synthesized in a triphosphoester form (step (e)) for characterization of its affinity and specificity.

Furthermore, the invention provides a useful method for isolation and characterization of the aptamers of the invention (FIG. 2). Briefly, an aptamer selection method, such as those described above, is applied to isolate the candidate aptamer structures using interactions of a random library of the phosphotriesterified oligonucleotides generated using the synthetic procedures described above and in FIG. 1. Once these aptamer candidates are obtained, they undergo deblocking. The sequences of the deblocked molecules are then determined using known methods as described above. Once these sequences are determined, the aptamers are synthesized as described above in FIG. 1.

Additionally, aptamers of the invention exhibit improved environmental stability. Without being limited by any particular theory or mechanism of action, it is believed that increased stability results from removal of the negative charge of the scissile phosphodiester bonds upon triesterification. More specifically, coordination of metal ion by the oxygen atoms of the scissile bond is a prerequisite of successful nuclease attack of oligonucleotides (Sokolowska M, Czapinska H, Bochtler M. Hpy188I-DNA pre- and post-cleavage complexes—snapshots of the GIY-YIG nuclease mediated catalysis. Nucleic Acids Res. 2011 March; 39(4):1554-64. Nowotny M, Gaidamakov S A, Crouch R J, Yang W. Crystal structures of RNase H bound to an RNA/DNA hybrid: substrate specificity and metal-dependent catalysis. Cell. 2005 Jul. 1; 121(7):1005-16.). The negatively charged oxygen atoms are necessary for coordination of the metal cations. Quenching the negative charge of the phosphate group oxygen atoms via triesterification prevents formation of this complex and disables enzymatic hydrolysis of the diphosphoester bonds. In addition, the third phosphoester functionality disrupts an intimate and precise spatial arrangement of the amino acids of the nuclease active site and the scissile phosphodiester bonds, which is required for successful nuclease attack of oligonucleotides.

Furthermore, as the additional chemical functionalities are included in the aptamer molecules, the resultant modified aptamers, in some instances, can potentially exhibit increased affinity (as compared to the non-modified molecules of aptamers) due to additional capabilities of binding to the anticipated aptamer targets via these additional functionalities.

In certain embodiments, the neutral nucleic acid ligands bind to CD271. Nucleic acid ligands that bind to CD271 are described for example in Gilman (PCT number PCT/US14/19284), the content of which is incorporated by reference herein in its entirety. Based on the known sequence of those nucleic acid ligands, neutral nucleic acid ligands having that same sequence can be synthesized. The advantage of the neutral nucleic acid ligands is that they will be neutral under physiological conditions as compared to the aptamers. The neutral nucleic acid ligands can be coupled to a drug for targeted to delivery to cells that express CD271, such as cancer cells. In other embodiments, the neutral nucleic acid ligands may be part of an implantable medical product, that includes a scaffold composed of a biocompatible material, and a plurality of morpholino ligands that binds to CD271. Once implanted, the neutral nucleic acid ligands will attract adult stem cells that express CD271. The increased rate of adult stem cell retention results in increased density of somatic tissue cells generated on the surface of the implant, providing an increased rate of tissue regeneration.

In certain embodiments, the neutral nucleic acid ligands bind to an infectious prion. Nucleic acid ligands that bind to infectious prion are described for example in Gilman (U.S. Patent application publication number 2011/0104668), the content of which is incorporated by reference herein in its entirety. Based on the known sequence of those nucleic acid ligands, neutral nucleic acid ligands having that same sequence can be synthesized. The advantage of the neutral nucleic acid ligands is that they will be neutral under physiological conditions as compared to the aptamers.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A nucleic acid ligand comprising repeating units of Formula I:

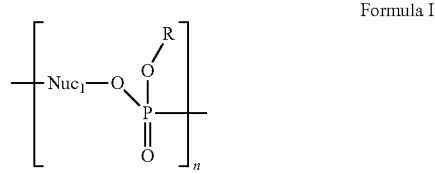

Formula I wherein:

Nuc$_1$ is a naturally or non-naturally occurring nucleoside that may be the same or different for each unit;

R is the same or different for each unit and is selected from the group consisting of an O-glycosylated biomolecule, an alcohol, an aromatic alcohol, a hydroxylated amino acid, an unnatural sugar, and a peptide containing hydroxylated amino acids; and n is an integer greater than 1.

2. The nucleic acid ligand according to claim 1, wherein the O-glycosylated biomolecule is selected from the group consisting of a fatty acid, a sugar, an amino sugar, an amino acid, and a sialic acid.

3. The nucleic acid ligand according to claim 1, wherein the nucleic acid ligand is single stranded.

4. The nucleic acid ligand according to claim 1, wherein the nucleic acid ligand is double stranded.

5. The nucleic acid ligand according to claim 1, wherein Nuc$_1$ is a deoxyribonucleic acid.

6. The nucleic acid ligand according to claim 1, wherein Nuc$_1$ is a ribonucleic acid.

7. The nucleic acid ligand according to claim 1, further comprising a detectable label.

8. The nucleic acid ligand according to claim 7, wherein the detectable label is an optically detectable label.

9. The nucleic acid ligand according to claim 8, wherein the optically detectable label is a fluorescent label.

\* \* \* \* \*